US00PP29841P2

(12) United States Plant Patent
O'Connell

(10) Patent No.: US PP29,841 P2
(45) Date of Patent: Nov. 13, 2018

(54) ***ECHEVERIA* PLANT NAMED 'ARCTIC LACE'**

(50) Latin Name: ***Echeveria* hybrid**
Varietal Denomination: Arctic Lace

(71) Applicant: Altman Specialty Plants, Inc, Vista, CA (US)

(72) Inventor: Renee O'Connell, Escondido, CA (US)

(73) Assignee: Altman Specialty Plants, Inc., Vista, CA (US)

( * ) Notice: Subject to any disclaimer, the term of this patent is extended or adjusted under 35 U.S.C. 154(b) by 0 days.

(21) Appl. No.: 15/732,294

(22) Filed: Oct. 19, 2017

(51) Int. Cl.
*A01H 5/12* (2018.01)

(52) U.S. Cl.
USPC ..... Plt./373

(58) Field of Classification Search
USPC ..... Plt./373
See application file for complete search history.

*Primary Examiner* — Annette H Para
(74) *Attorney, Agent, or Firm* — Cassandra Bright

(57) ABSTRACT

A new and distinct *Echeveria* cultivar named 'Arctic lace' is disclosed, characterized by rosettes of frosted baby blue leaves with an unusual leaf shape that is uplifted towards the center of the plant. Foliage is anfractuously crenulate with a hyaline margin. The new cultivar is robust growing enabling faster production times for finished commercial pots. The new variety is an *Echeveria*, part of the Crassulaceae complex that includes *Aeonium, Crassula, Graptopetalum, Pachyphytum, Sedum* and others. *Echeveria* is a popular genus, typically produced as container plants for the patio or as landscape plants, as a variety of ornamental purposes.

2 Drawing Sheets

Latin name of the genus and species: *Echeveria* hybrid.
Variety denomination: 'ARCTIC LACE'.

BACKGROUND OF THE INVENTION

The new cultivar, *Echeveria* 'ARCTIC LACE', is the product of a planned breeding program. The new variety originated from a cross pollination of the proprietary, unpatented, seed parent, *Echeveria* 'Aqua 4' with the pollen parent an unpatented, proprietary variety of *Echeveria* referred to as 'Dop11'. The cross pollination was made during September, 2013 in Vista, Calif., at a commercial greenhouse. The new cultivar 'ARCTIC LACE' was discovered by the inventor, Renee O' Connell, in June, 2014, in Vista, Calif. at a commercial greenhouse.

Asexual reproduction of the new cultivar 'ARCTIC LACE' was first performed in Vista, Calif., at a commercial greenhouse, by terminal vegetative cuttings in May, 2014. *Echeveria* 'ARCTIC LACE' has since produced multiple generations and has shown that the unique features of this cultivar are stable and reproduced true to type.

SUMMARY OF THE INVENTION

The cultivar 'ARCTIC LACE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ARCTIC LACE'. These characteristics in combination distinguish 'ARCTIC LACE' as a new and distinct *Echeveria* cultivar:

1. Rosettes of frosted baby blue leaves with an unusual leaf shape that is uplifted towards the center of the plant.

2. The leaves with an anfractuously crenulate, hyaline margin.
3. Leaves distinctively upturned towards the center of the rosette, caused by the anfractuous margins pushing the leaf apices inward.
4. Fast growing as compared with many other *Echeverias*, enhancing production times in the commercial nursery.
5. *Echeveria* 'Arctic Lace', with its unusual leaf shape that is uplifted towards the center of the plant, in combination with the anfractuous, hyaline margins displays an overall appearance of "lace", not observed with other *Echeverias.*
6. *Echeveria* 'Arctic Lace', due to its anfractuous, hyaline margins and icy blue color, provides an excellent accent for holiday table centerpieces, bridal bouquets and succulent arrangements, as compared to many other *Echeverias.*

PARENTAL COMPARISON

Plants of the new cultivar are similar to plants of the seed parent, in most horticultural characteristics, however, plants of the new cultivar differ in the following;

1. *Echeveria* 'Arctic Lace' displays leaves that flare at the apices, and fold slightly downward at the sides to create the appearance of a "fluted" leaf, whereas *Echeveria* 'Aqua 4' does not.
2. *Echeveria* 'Arctic Lace' exhibits less afractuity than does the seed parent *Echeveria* 'Aqua 4'.
3. The hyaline margin of the leaves of *Echeveria* 'Arctic Lace' is wider than the hyaline margin of *Echeveria* 'Aqua 4'.
4. *Echeveria* 'Arctic Lace' grows faster than *Echeveria* hybrid 'Arctic Lace'.

5. *Echeveria* 'Arctic Lace' displays a morphology of upswept, fluted leaves, whereas *Echeveria* 'Aqua 4' does not exhibit upswept, fluted leaves.

Plants of the new cultivar are similar to plants of the pollen parent, in most horticultural characteristics, however, plants of the new cultivar differ in the following;

1. *Echeveria* 'Arctic Lace' displays very anfractuous leaf margins, whereas *Echeveria* 'Dop11' does not.
2. *Echeveria* 'Arctic Lace' exhibits hyaline leaf margins, whereas *Echeveria* 'Dop11' shows no differentiation in color between leaf and leaf margin.
3. *Echeveria* 'Arctic Lace' has flowers that are smaller than those of *Echeveria* 'Dop11'.
4. *Echeveria* 'Arctic Lace' grows somewhat taller than *Echeveria* 'Dop11', with more upswept appearance to the apical tips of the leaves, whereas *Echeveria* 'Dop11' forms a more flattened rosette, with less upswept curvature of the leaves.

COMMERCIAL COMPARISON

The new cultivar 'Arctic Lace' can be compared to the unpatented commercial variety *Echeveria* 'Topsy Turvy'. Plants of *Echeveria* 'Topsy Turvy' are similar to plants of the new cultivar 'Arctic lace' in most horticultural characteristics. However, the new cultivar 'Arctic Lace' differs in the following:

1. *Echeveria* 'Arctic Lace' displays anfractuous leaf margins whereas the leaf margins of *Echeveria* 'Topsy Turvy' are entire, and devoid of anfractuitous crenations.
2. *Echeveria* 'Arctic Lace' exhibits hyaline leaf margins, whereas the leaf margins of *Echeveria* 'Topsy Turvy' are the same color as the rest of the leaf.
3. *Echeveria* 'Arctic Lace' is faster growing than *Echeveria* 'Topsy Turvy'
4. *Echeveria* 'Arctic Lace' does not have a "groove" down the center of the bottom of each leaf, whereas *Echeveria* 'Topsy Turvy' has a groove down the center of the bottom of each leaf.
5. *Echeveria* 'Arctic Lace' does not have prominent bracts on the inflorescence, whereas *Echeveria* 'Topsy Turvy' has prominent bracts on the inflorescence.
6. *Echeveria* 'Arctic Lace' has smaller flowers than those of *Echeveria* 'Topsy Turvy'

The new cultivar 'Arctic Lace' can be compared to the unpatented commercial variety *Echeveria* 'Perle von Nurnberg'. Plants of *Echeveria* 'Perle von Nurnberg' are similar to plants of the new cultivar 'Arctic Lace' in most horticultural characteristics. However, plants of the new cultivar 'Arctic Lace' differ in the following:

1. *Echeveria* hybrid 'Arctic Lace' forms rosettes of icy blue, whereas the rosettes of *Echeveria* 'Perle von Nurnberg' are dusty violet in color.
2. *Echeveria* hybrid 'Arctic Lace' displays very anfractuous leaf margins, whereas the margins of *Echeveria* hybrid 'Perle von Nurnberg' are entire, and are devoid of crenation.
3. The rosette of *Echeveria* hybrid 'Arctic Lace' displays an upswept appearance, whereas the rosette of *Echeveria* 'Perle von Nurnberg' is more flattened in appearance.

BRIEF DESCRIPTION OF THE PHOTOGRAPHS

The accompanying photographs illustrate in full color typical plants of 'ARCTIC LACE' grown in a greenhouse in Vista, Calif. The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of the new *Echeveria* plant. The following photographs depict plants grown under natural light conditions of 2500-4000 foot-candles. Temperatures ranged from −1° C. to 29° C. night and day. No artificial light, photoperiodic treatments or chemical treatments were given to the plants.

DETAILED BOTANICAL DESCRIPTION

Figure 1:
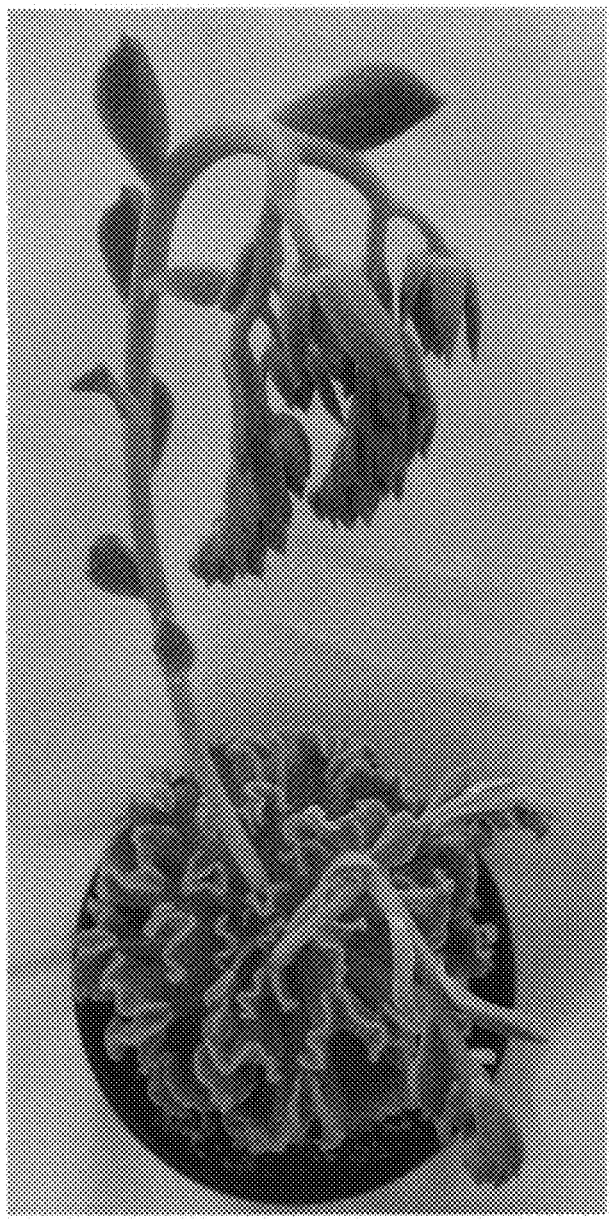
FIG. 1 illustrates in full color the top view of a rosette typical of plants of *Echeveria* 'Arctic lace' grown in a greenhouse in Vista, Calif. with a developing inflorescence.
Figure 2:
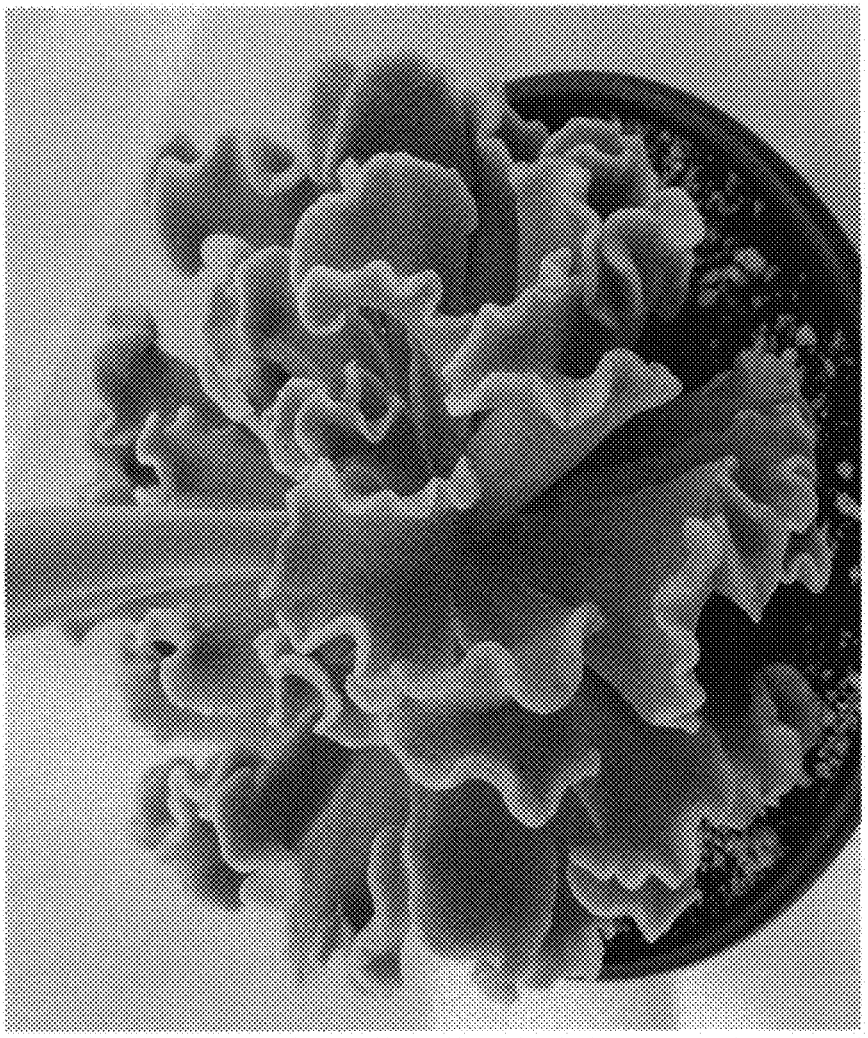
FIG. 2 illustrates in full color a close up view of a rosette typical of plants of *Echeveria* 'Arctic lace' grown in a greenhouse in Vista, Calif.

In the following description, color references are made to The Royal Horticultural Society Colour Chart, 2007 except where general terms of ordinary dictionary significance are used. The following observations and measurements describe 'Arctic lace' plants in a commercial greenhouse in Vista, Calif. Temperatures ranged from −1° C. to 29° C. night and day. No artificial light, photoperiodic treatments or chemical treatments were given to the plants. Natural light conditions were approximately 2500 to 4000 fc of light. Measurements and numerical values represent averages of typical plant types.

Botanical classification: *Echeveria* hybrid 'ARCTIC LACE'.

PROPAGATION

Type of propagation typically used: Terminal vegetative cuttings.

Time to initiate roots: About 11 days at approximately 24° C.

Root description: Fibrous, light tan, not accurately measured with the R.H.S. chart.

PLANT

Age of plant described: Approximately 4 months from a cutting.

Container size of the plant described: 1 gallon.

Growth habit: Upright rosulate plant.

Height: Approximately 10 cm to top of highest leaf. Approximately 40 cm to 55 cm to top of highest inflorescence.

Plant spread: Approximately 16.0 cm.

Growth rate: Moderate.

Branching characteristics: Not typically observed.

FOLIAGE

Leaf:

*Arrangement.*—Rosulate.

*Average length.*—7 cm.

*Average width.*—2.5 cm.

*Width at base.*—Average 1.0 cm.

*Thickness of leaf.*—Thickest section, near base mm.

*Shape of blade*.—Spatulate.

*Aspect*.—Leaf folds downward, so extremely it is almost completed folded in half. Apical margin extremely undulate.

*Apex*.—Irregular, large crenations with a single, sharp mucronate tip. Mucronate tip about 2 mm long, often breaking off.

*Base*.—Broad attenuate.

*Margin*.—Anfractuous, upper ⅓ irregularly crenate with deep undulation. Entire along lower ⅔.

*Texture of top surface*.—Slightly glaucous.

*Texture of bottom surface*.—Slightly glaucous.

*Appearance of top surface*.—Matte.

*Appearance of bottom surface*.—Matte.

*Quantity of leaves per plant*.—Average range 25 to 40.

*Color*.—Young foliage upper side: Near RHS Greyed-Green 191B. Very fine apical margin coloration near Yellow-Green 150D, slightly flushed Orange-Red N34C. Glaucous layer over entire surface colored near Greyed-Green 189D. Young foliage under side: Near RHS Greyed-Green 191B. Very fine apical margin coloration near Yellow-Green 150D, slightly flushed Orange-Red N34C. Glaucous layer over entire surface colored near Greyed-Green 189D. Mature foliage upper side: Near RHS Greyed-Green 191B. Strong apical margin coloration near Red 46C. Hyaline margin near Yellow-Orange 18A, fading out to 18B. Glaucous layer over entire surface colored near Greyed-Green 189D. Mature foliage, under side: Near RHS Greyed-Green 191B. Strong apical margin coloration near Red 46D. Hyaline margin near Yellow-Orange 18A, fading out to 18B. Glaucous layer over entire surface colored near Greyed-Green 189D.

FLOWER

Natural flowering season: Spring through Summer.

Inflorescence type and habit: Erect, composed of several simple or bifurcate cincinni, each cincinnus typically with 5 to 8 flowers and about 3 buds.

Rate of flower opening: About 3 to 7 days from bud stage to open flower, depending on environmental conditions.

Flower longevity on plant: 3-6 days, depending upon ambient temperatures.

Quantity of flowers: About 20 to 35 individual flowers and 15 to 30 buds.

*Total inflorescence size*.—Height: Approximately 10 to 20 cm. Width: Approximately 8 to 15 cm.

*Corolla*.—Arrangement: Pentagonal, fused. Apex flaring out. Size: Length: Approximately 1.6 cm. Width: Approximately 1.5 cm at widest point. Lobe Length: Approximately 0.7 cm. Lobe width: Approximately 0.3 cm.

*Petals*.—Margin: Entire. Shape: Unfused section narrow deltate. Apex: Narrow acute. Base: Fused, approximately ¾ entire length. Texture: Glabrous.

Color:

*When opening*.—Petal color, outer surface: Near RHS Orange-Red 35C, flushed Yellow 13B. Inner surface: Base Orange 27D, apex yellow-orange 23A.

*Fully opened*.—Outer surface: Near Red 38B and 54C, present individually as streaks. Flushed near Yellow-Orange 15B. Inner surface: Near Red 38B and 54C, present individually as streaks. Heavily flushed near Yellow-Orange 15B. Color Changes when Aging: Flower contracts, making inner surface impossible to see. Outer surface: Near Red 51C.

Bud: (Near opening):

*Shape*.—Conical.

*Length*.—Approximately 1.3 cm.

*Diameter*.—Approximately 0.8 cm.

*Color*.—Near Red 51D, lightly flushed Greyed-Green 194D.

Sepals:

*Length*.—6 to 12 mm.

*Width*.—3 to 4 mm.

*Margin*.—Entire.

*Shape*.—Narrow deltate.

*Apex*.—Acute.

*Base*.—Truncate.

*Texture*.—Glabrous, upper and lower surfaces.

*Appearance*.—Very slightly shiny, upper and lower surfaces.

*Color*.—Outer: Near Greyed-Orange 166B, base near Green 138B. Inner: Near RHS Green 138A apex near Greyed-Red 178A.

Peduncle:

*Length*.—Average range 28 to 32 cm.

*Width*.—Approximately 7 mm.

*Strength*.—Strong.

*Texture*.—Glabrous.

*Color*.—Base near RHS Greyed-Red 180D, flushed. Greyed-Purple N187D.

Pedicels:

*Length*.—Approximately 0.4 cm.

*Width*.—Approximately 0.2 cm.

*Strength*.—Strong, flexible.

*Texture*.—Glabrous.

*Color*.—Near RHS Red 51C.

Fragrance: None detected.

REPRODUCTIVE ORGANS

Stamens: (Androecium).

*Number*.—Average 8 to 10.

*Filament length*.—Approximately 0.4 cm.

*Filament color*.—Near RHS White N155D.

*Anther length*.—0.3 cm.

*Anther color*.—Near RHS Yellow 1C.

*Anther shape*.—Oblong.

*Pollen color*.—Near RHS Yellow 5D.

*Pollen quantity*.—Scant.

Pistil: (Gynoecium).

*Number*.—Average 5.

*Length*.—Approximately 1.4 cm.

*Style color*.—Near White N155D.

*Stigma*.—Shape: Linear. Color: Near RHS Red 55A. Ovary Color: Near RHS White 155C.

OTHER CHARACTERISTICS

Fruits and seeds: Typical to Genus. Minute, less than 1 mm dry seeds. Colored between black and brown, too small to accurately measure with color chart.

Temperature tolerance: Tolerates temperatures from approximately −2° C. to at least 35° C.

Disease/pest resistance: Neither resistance or susceptibility to normal diseases and pests of *Echeveria* has been observed.

Drought tolerance: Tolerates at least 3 weeks of high temperatures without supplemental water, showing no serious damage to plant.

What is claimed is:

1. A new and distinct cultivar of *Echeveria* plant named 'ARCTIC LACE' as herein illustrated and described.

* * * * *